(12) United States Patent
Hashimoto

(10) Patent No.: US 6,398,407 B2
(45) Date of Patent: Jun. 4, 2002

(54) TEMPERATURE DETECTOR FOR EXHAUST GAS SENSOR

(75) Inventor: Kohji Hashimoto, Tokyo (JP)

(73) Assignee: Mitsubishi Denki Kabushiki Kaisha, Tokyo (JP)

(*) Notice: Subject to any disclaimer, the term of this patent is extended or adjusted under 35 U.S.C. 154(b) by 0 days.

(21) Appl. No.: 09/732,745

(22) Filed: Dec. 11, 2000

(30) Foreign Application Priority Data

Jun. 7, 2000 (JP) ........................................ 2000-170843

(51) Int. Cl.$^7$ ........................ G01K 13/02; G01K 15/00; G01N 27/27
(52) U.S. Cl. ........................ 374/144; 374/148; 374/183; 702/99; 702/133
(58) Field of Search ................................ 374/144, 145, 374/148, 142, 183; 702/130, 133, 99; 477/97, 98; 123/198 D

(56) References Cited

U.S. PATENT DOCUMENTS

| | | | | |
|---|---|---|---|---|
| 5,129,258 A | * | 7/1992 | Homeyer | 374/144 |
| 5,219,228 A | * | 6/1993 | Ker et al. | 374/144 |
| 5,647,668 A | * | 7/1997 | Schnaibel et al. | 374/144 |
| 6,088,661 A | * | 7/2000 | Poublon | 374/144 |
| 6,200,021 B1 | * | 3/2001 | Mitsutani et al. | 374/145 |
| 2002/0008100 A1 | * | 1/2002 | Hosoya et al. | 374/144 |

FOREIGN PATENT DOCUMENTS

| | | | | |
|---|---|---|---|---|
| JP | 59196454 A | * | 11/1984 | ................ 374/142 |
| JP | 1-172746 | | 7/1989 | ......... G01N/27/46 |
| JP | 7-119736 | | 12/1995 | ......... G01N/27/41 |
| JP | 8-313476 | | 11/1996 | ......... G01N/27/409 |
| JP | 9-292364 | | 11/1997 | ......... G01N/27/41 |

\* cited by examiner

*Primary Examiner*—Diego Gutierrez
*Assistant Examiner*—Stanley J. Pruchnic, Jr.
(74) *Attorney, Agent, or Firm*—Sughrue Mion, PLLC

(57) ABSTRACT

A temperature detector for an exhaust gas sensor comprises: an exhaust gas sensor 2 for detecting a concentration of oxygen contained in exhaust gas discharged from an internal combustion engine; a temperature sensor 6 for measuring an environmental temperature which is substantially the same as the exhaust gas sensor 2; a resistance measuring means 12 for measuring an internal resistance value of the exhaust gas sensor 2; a timer means 10 for measuring an operation stop time of the internal combustion engine; and a control means 8 for detecting the internal resistance value of the exhaust gas sensor 2 and the environmental temperature at each operation starting point when a period of operation stop conducted by the timer means 10 is longer than a predetermined period, for calculating a characteristic of the internal resistance value versus the temperature of the exhaust gas sensor 2 from both the internal resistance of the exhaust gas sensor and the environmental temperature, for renewing and storing them, and for calculating a temperature of the exhaust gas sensor 2 from the internal resistance of the exhaust gas sensor 2 in operation, which is measured in operation, and also from the characteristic of the internal resistance value versus the temperature.

5 Claims, 3 Drawing Sheets

TEMPERATURE DETECTOR FOR EXHAUST GAS SENSOR

BACKGROUND OF THE INVENTION

1. Field of the Invention

The present invention relates to a temperature detector to detect a temperature of a sensor element in such a manner that an internal resistance value of an exhaust gas sensor to detect a concentration of oxygen contained in exhaust gas discharged from an internal combustion engine is measured and the thus measured internal resistance is converted into the temperature of the sensor element.

2. Description of the Related Art

A technique is well known in which a concentration of oxygen contained in exhaust gas discharged from an internal combustion engine is detected, and the exhaust gas is purified and the rate of fuel consumption of the internal combustion engine is improved by conducting feedback control with an air fuel ratio of mixture supplied to the internal combustion engine according to the thus detected concentration of oxygen. This technique is widely applied to internal combustion engines for automobile use. Concerning the exhaust gas sensor to detect the concentration of oxygen, it is necessary to keep the temperature in an activating region so that the detection characteristic of the oxygen concentration can be stabilized. Therefore, a heater is incorporated into the exhaust gas sensor and an electrical current is supplied to the heater being controlled so as to keep the temperature of the exhaust gas sensor at a predetermined value. In order to control an intensity of this electrical current, it is necessary to measure the temperature of the sensor element. With respect to this temperature measuring technique, various methods have been disclosed until now.

For example, according to Japanese Unexamined Patent Publication No. 9-292364, as the method of measuring the internal resistance value by which the internal resistance value of the exhaust gas sensor is detected so as to calculate the temperature of the sensor element from the thus measured internal resistance value, there is disclosed a technique in which a voltage impressed upon the exhaust gas sensor in the case of detecting the concentration of oxygen is changed over to a voltage used for detecting a resistance value by a predetermined time constant, and the internal resistance value of the exhaust gas sensor is detected from a state of a change in the voltage and current. According to Japanese Unexamined Patent Publication No. 7-119736, there is disclosed a technique in which a nonlinear type exhaust gas sensor, which is called a λ type exhaust gas sensor, is used and the temperature of the exhaust gas sensor is indirectly estimated by using parameters of the running state of an internal combustion engine such as a quantity of sucked air and a rotating speed.

Further, Japanese Unexamined Patent Publication No. 8-313476 discloses a technique by which the temperature of a sensor element is indirectly estimated in such a manner that a heater resistance is detected from a voltage and current of a heater arranged close to the exhaust gas sensor so that a heater temperature is calculated. Further, Japanese Unexamined Patent Publication No. 1-172746 discloses a technique by which the temperature of an exhaust gas sensor, which is arranged close to a heater, is indirectly estimated in such a manner that a target resistance value of the heater according to a flow rate of exhaust gas, that is, a target of a temperature of the heater is set and an electrical current is controlled so that the heater resistance value can be the target value.

In the prior art described above in which the temperature of an exhaust gas sensor is indirectly measured from the resistance value of a heater, a correlation between the heater temperature and the exhaust gas sensor is changed by the flow rate and the temperature of exhaust gas. Therefore, even if the target resistance value of the heater is set according to the flow rate of exhaust gas as disclosed in Japanese Unexamined Patent Publication No. 1-172746, it is impossible to detect an accurate temperature of the exhaust gas sensor. In the method described in Japanese Unexamined Patent Publication No. 9-29236 in which a temperature is calculated by measuring an internal resistance value of the exhaust gas sensor itself, the internal resistance value and the correlation between the internal resistance value and the temperature are greatly changed by the fluctuation and the change with age. Therefore, it is impossible to detect an accurate temperature only by measuring the internal resistance value and converting it into temperature.

SUMMARY OF THE INVENTION

The present invention has been accomplished to solve the above problems. It is an object of the present invention to provide a temperature detector for an exhaust gas sensor by which a temperature can be accurately detected by conducting measurement while the fluctuation of the internal resistance value is being corrected and also the change with age is being corrected, and further a warning against deterioration is outputted when the internal resistance value is greatly changed with age.

A temperature detector for an exhaust gas sensor comprises: an exhaust gas sensor for detecting a concentration of oxygen contained in exhaust gas discharged from an internal combustion engine; a temperature sensor for measuring an environmental temperature which is substantially the same as the exhaust gas sensor; a resistance measuring means for measuring an internal resistance value of the exhaust gas sensor; a timer means for measuring an operation stop time of the internal combustion engine; and a control means for detecting the internal resistance value of the exhaust gas sensor and the environmental temperature at each operation starting point when a period of operation stop conducted by the timer means is longer than a predetermined period, for calculating a characteristic of the internal resistance value versus the temperature of the exhaust gas sensor from both the internal resistance of the exhaust gas sensor and the environmental temperature, for renewing and storing them, and for calculating a temperature of the exhaust gas sensor from the internal resistance of the exhaust gas sensor in operation, which is measured in operation, and also from the characteristic of the internal resistance value versus the temperature.

A temperature detector for an exhaust gas sensor comprises: an exhaust gas sensor for detecting a concentration of oxygen contained in exhaust gas discharged from an internal combustion engine; a temperature sensor for measuring an environmental temperature which is substantially the same as the exhaust gas sensor; a resistance measuring means for measuring an internal resistance value of the exhaust gas sensor; a timer means for measuring an operation stop time of the internal combustion engine; and a control means for detecting the internal resistance value of the exhaust gas sensor and the environmental temperature at each operation starting point when a period of operation stop conducted by the timer means is longer than a predetermined period, for calculating a characteristic of the internal resistance value versus the temperature of the exhaust gas sensor from both the internal resistance of the exhaust gas sensor and the environmental temperature, for renewing and storing them, and for calculating a temperature of the exhaust gas sensor from the internal resistance of the exhaust gas sensor in operation, which is measured in operation, and also from the characteristic of the internal resistance value versus the temperature, wherein the control means has a discriminating function to discriminate an operation state between a test mode and an operation mode, the control means stores an internal resistance value of the exhaust gas sensor, which has been measured in the first motion of the operation mode after the completion of the test mode, as a reference value, and the deterioration of the exhaust gas sensor is judged when this reference value is compared with the internal resistance value of the exhaust gas sensor measured at each operation staring point.

In a temperature detector for an exhaust gas sensor, the temperature sensor is an outside air temperature sensor mounted on a vehicle or a cooling water temperature sensor.

In a temperature detector for an exhaust gas sensor, the timer means for measuring an operation stop period utilizes a signal obtained from a digital clock mounted on a vehicle.

In a temperature detector for an exhaust gas, the timer means for measuring an operation stop period utilizes a heat-radiating time in which heat is radiated so that a heating section of the temperature detector can be cooled to a predetermined temperature after the stop of operation.

DETAILED DESCRIPTION OF THE PRESENT INVENTION

Embodiment 1

Figure 1:
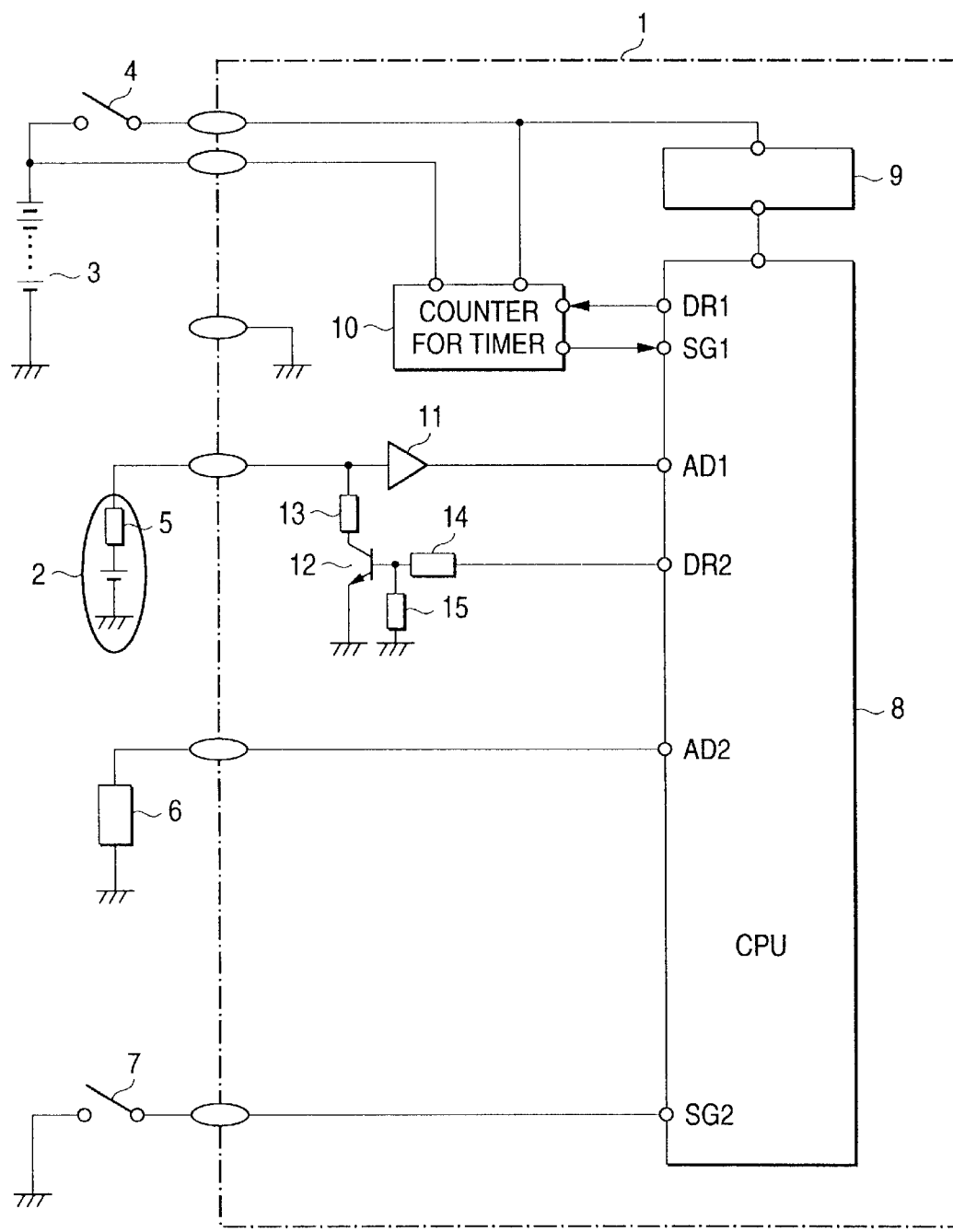
FIG. 1 is a circuit diagram of a temperature detector for an exhaust gas sensor of Embodiment 1 of the present invention.
Figure 2:
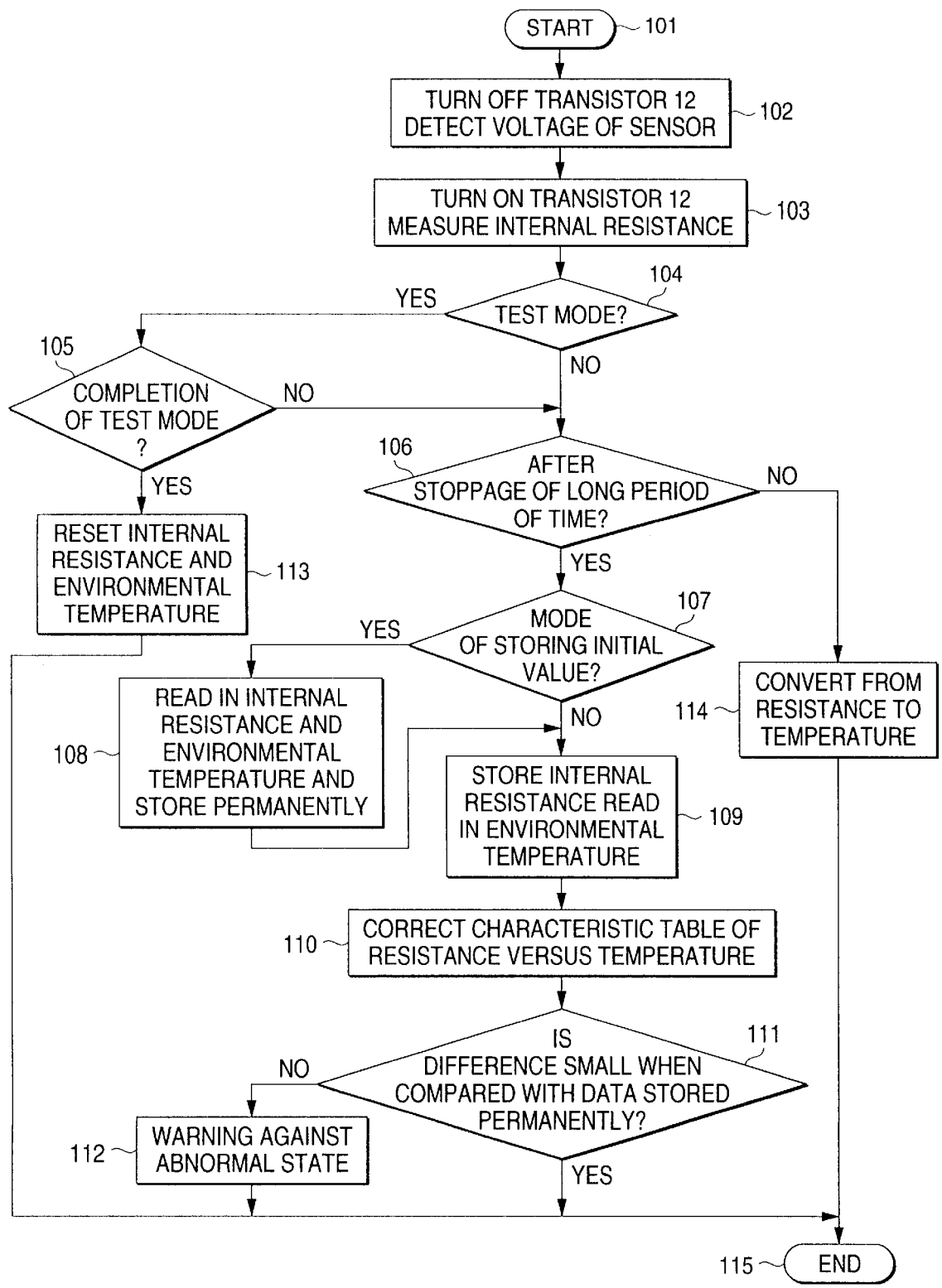
FIG. 2 is a flow chart for explaining the operation of the temperature detector for an exhaust gas sensor of Embodiment 2 of the present invention.

FIG. 1 is a circuit diagram of a temperature detector for an exhaust gas sensor of Embodiment 1 of the present invention, and FIG. 2 is a flow chart for explaining the operation of the temperature detector. In FIG. 1, reference numeral 1 is a temperature detector for detecting the temperature of the exhaust gas sensor 2 and for controlling a heater not shown which is incorporated into the exhaust gas sensor 2. Reference numeral 3 is a battery mounted on a vehicle and used for feeding electrical power to the temperature detector 1. Reference numeral 4 is a key switch. Reference numeral 5 is an internal resistance which is schematically illustrated. Reference numeral 6 is a temperature sensor for measuring the temperature of outside air or the temperature of cooling water. Reference numeral 7 is a mode switch for switching the temperature detector 1 between the practical operation mode and the test mode. This test mode is used when the temperature detector 1 itself is inspected in the delivery inspection.

Reference numeral 8 is a micro-processor, which will be referred to as CPU hereinafter, which functions as a control means housed in the temperature detector 1. Reference numeral 9 is a constant voltage power source for supplying a constant voltage to CPU 8, for example, for supplying a constant voltage of DC 5V to CPU 8. Reference numeral 10 is a counter for the timer. CPU 8 is supplied with electrical power from the battery 3 via the key switch 4 and the constant voltage power supply 9. The counter 10 is always supplied with electrical power from the battery 3 without the intervention of the key switch 4. On the other hand, an ON and OFF signal of the key switch 4 is inputted into the counter 10. When the counter receives a signal of opening the circuit from the key switch 4, it generates a clock pulse signal and starts counting. When the key switch 4 closes the circuit, by a reading signal sent from output terminal DR1 of CPU 8, a counted time signal obtained in a period in which the circuit is opened is outputted to signal input terminal SG1 of CPU 8, and at the same time the counted value is reset.

Reference numeral 11 is an amplifier for amplifying an output of the exhaust gas sensor 2 and giving it to input terminal AD1 for A/D conversion of CPU 8. Reference numeral 12 is a transistor for detecting an internal resistance value which is driven by a signal sent from output terminal DR2 of CPU 8, wherein this transistor 12 connects a load resistance 13 with the exhaust gas sensor 2. Reference numeral 14 is a base resistance of the transistor 12 arranged in a signal path from output terminal DR2 of CPU 8. Reference numeral 15 is a ballast resistance arranged between the base of the transistor 12 and the emitter. The temperature sensor 6 is connected with input terminal AD2 for A/D conversion of CPU 8. The mode switch 7 is connected with signal input terminal SG2 of CPU 8. In this connection, although not shown in the drawing, a memory means is housed in CPU 8 or alternatively attached to CPU 8 from the outside.

In the above temperature detector for an exhaust gas sensor of Embodiment 1 of the present invention, CPU 8 operates as shown in the flow chart of FIG. 2. As shown in FIG. 2, in step 101, the key switch 4 is operated so as to start operation. Then, in step 102, CPU 12 turns off the transistor 12 for a predetermined period of time by a signal sent from output terminal DR2, and an output voltage in the case of no load of the exhaust gas sensor 2 is taken into input terminal AD1 of CPU 8 via the amplifier 11. This input voltage of AD1 corresponds to a concentration of oxygen contained in exhaust gas which is detected by the exhaust gas sensor 2.

Next, in step 103, the transistor 12 is turned on for a predetermined period of time by a signal sent from output terminal DR2, and an output voltage in the case of loading, which is divided by the internal resistance 5 of the exhaust gas sensor 2 and the load resistance 13, is taken into input terminal AD1 via the amplifier 11, and the resistance value of the internal resistance 5 is calculated. In this case, the following equation (1) can be obtained, $$E1 = E0 \times R1/(R1+R0) \tag{1}$$

where E0 is an output voltage in the case of no load of the exhaust gas sensor 2 obtained in step 102, E1 is an output voltage in the case of a load of the exhaust gas sensor 2 obtained in step 103, R1 is a resistance value of the load resistance 13, and R0 is a resistance value of the internal resistance 5 of the exhaust gas sensor 2. Internal resistance value R0 of the exhaust gas sensor 2 can be calculated by the above equation (1).

The value of internal resistance R0 is changed as an exponential function of an inverse number of absolute temperature of the exhaust gas sensor 2 and expressed by the following equation (2).

$$R0 = K1 \exp(K2/T) \tag{2}$$

In the above equation, K1 and K2 are constants, and T is an absolute temperature. Constant K1 is greatly changed by the fluctuation of a product of the exhaust gas sensor 2 and the change with age. However, constant K2 is a known constant that is determined by the type of the exhaust gas sensor 2. Therefore, constant K2 is seldom changed by the fluctuation and the change with age.

When the value of internal resistance R0 is calculated in step 103, the program proceeds to step 104. In step 104, it is judged whether the mode switch 7 is in the test mode or the practical operation mode. When it is judged that the mode switch 7 is in the test mode, the program proceeds to step 105. However, when it is judged that the test mode has not been completed yet and also when it is judged in step 104 that the mode switch 7 is in the practical operation mode, the program proceeds to step 106. In step 106, CPU 8 sends a signal from DR1 terminal to the counter 10 used for the timer, and a counted time signal sent from the counter 10 used for the timer is taken into SG1, and an operation stop time of an internal combustion engine from when the key switch 4 is turned off to when the key switch 4 is turned on next time is read in. Then it is judged whether or not this operation stop time is not less than a predetermined value.

When it is judged that the operation stop time is not less than a predetermined value, the program proceeds to step 107, and it is judged whether or not it is in the initial value storing mode. In the case where it is after the internal combustion engine has been stopped for not less than a predetermined period of time and it is the first motion in the practical operation mode, or in the case where the initial value is not stored in the memory means, it is judged to be in the initial value storing mode. Due to the above judgment, the program proceeds to step 108, and the value of internal resistance of the exhaust gas sensor 2 obtained in step 103 and the environmental temperature measured by the temperature sensor 6 are stored in the memory means as the initial values. Until operation is made in step 113 described later and until a reset means not shown is operated when he deteriorated exhaust gas sensor 2 is replaced with a new one, these initial values are kept being permanently stored. Unless these initial values are reset, it is not judged in step 107 that it is in the initial value storing mode.

If the initial values are stored, that is, unless it is a first motion in the practical operation mode, the program proceeds from step 107 to step 109, and the value of internal resistance of the exhaust gas sensor 2 obtained in step 103 and the environmental temperature measured by the temperature sensor 6 are renewed and stored. Next, in step 110, a table of the value of internal resistance versus the temperature is made from the value of internal resistance of the exhaust gas sensor 2 renewed and stored in step 109 and the environmental temperature. In this step 109, the key switch 4 is turned on. When it is judged that the operation stop time of the internal combustion engine is longer than a predetermined time, the internal resistance of the exhaust gas sensor 2 and the environmental temperature measured by the temperature sensor 6 at this point of time are surely renewed and stored. In the next step 110, the table of the internal resistance versus the temperature is also renewed.

Successively, the program proceeds to step 111. In step 111, the initial value of the internal resistance of the exhaust gas sensor 2 stored in step 108 is converted into a value according to the environmental temperature renewed and stored in step 109. Thus converted value of resistance and the value of resistance of the exhaust gas sensor 2 of this time, which is renewed and stored in step 109, are compared with each other. When there is a difference bigger than a predetermined value between them, the program proceeds to step 112, and a warning is outputted so as to report the occurrence of an abnormal state. This warning to report the occurrence of an abnormal state is a warning to report the deterioration of the exhaust gas sensor 2. This warning to report the occurrence of an abnormal state is outputted from CPU 8 to a light emitting diode, which is a display means not shown in the drawing, so that the warning can be displayed by the light emitting diode.

When the difference between them is smaller than a predetermined value in step 111, the program proceeds to step 115 as it is, and the routine is completed and the program returns to the step 101 so as to start the next routine. In this routine after the second time, it is judged in step 106 that it is not after a long stop of operation. Therefore, the program proceeds to step 114. In step 114, the temperature of the exhaust gas sensor 2 at this point of time is calculated from the value of internal resistance of the exhaust gas sensor 2 obtained in step 103 and the table of the internal resistance value versus the temperature made and stored in step 110, and data necessary for controlling an electrical current is provided so as to control the heater to heat the exhaust gas sensor 2. Then the program returns from step 115 to step 101. As described above, the table of the internal resistance value versus the temperature is always renewed in the operation after the internal combustion engine is stopped for a period of time longer than a predetermined period of time, and correction is made for the change of the internal resistance value with age.

In step 104, it is judged to be the test mode only in the case of delivery or replacement of parts. In this case, the program proceeds to step 105. When it is judged in step 105 that the test mode is completed, the program proceeds to the next step 113. In step 113, the initial value stored in step 108 is reset in accordance with the completion of the test. However, in the test mode, the signals of the exhaust gas sensor 2 and the temperature sensor 6 are not used, but a pseudo-signal is inputted and tested. Therefore, this pseudo-signal is reset, and the initial values of the exhaust gas sensor 2 and the temperature sensor 6 are stored in the first motion of the next operation mode. In this connection, as described above, these initial values are the reference value of judgment with respect to the deterioration of the exhaust gas sensor 2.

In step 110, a table of the internal resistance versus the temperature from the minimum use environmental temperature (for example, $-40°$ C.) to the practical temperature ($700°$ C.) is made. In this case, in the same manner as that of the above equation (2), the calculation is made by the formula of $Rs=K1\ exp(K2/T1)$.

Accordingly, K1 can be obtained by the following equation.

$$K1 = Rs/\exp(K2/T1) \tag{3}$$

When the temperature is Tn, the value of internal resistance Rn can be calculated by the following equation.

$$\begin{aligned}Rn &= K1\exp(K2/Tn) \\ &= Rs\exp(K2/Tn)/\exp(K2/T1)\end{aligned} \tag{4}$$

In the above equation, constant K2 is determined by the type of the exhaust gas sensor 2, which seldom fluctuates, and the change with age is very small. Constant K1 changes greatly due to fluctuation, and the change with age of constant K1 is large. This constant K1 is excluded from the equation. Therefore, the value of resistance Rn can be accurately calculated as a function of only temperature with respect to the value of resistance Rn, and only constant K2 is stored for calculation.

According to the structure explained above, the counter 10 used for the timer is arranged in the temperature detector 1. However, it is possible to adopt the following structure. Time at which the key switch 4 has opened the circuit is detected and stored by using the output of the digital clock mounted on the vehicle, and a time difference can be calculated when the key switch 4 has closed the circuit again. By this time difference, it is possible to judge that the internal combustion engine has stopped over a long period of time. The exhaust gas sensor 2 is not limited to the nonlinear type exhaust gas sensor, but it is possible to use a liner type exhaust gas sensor having two terminals or three terminals and detect its internal resistance.

Embodiment 2

Figure 3:
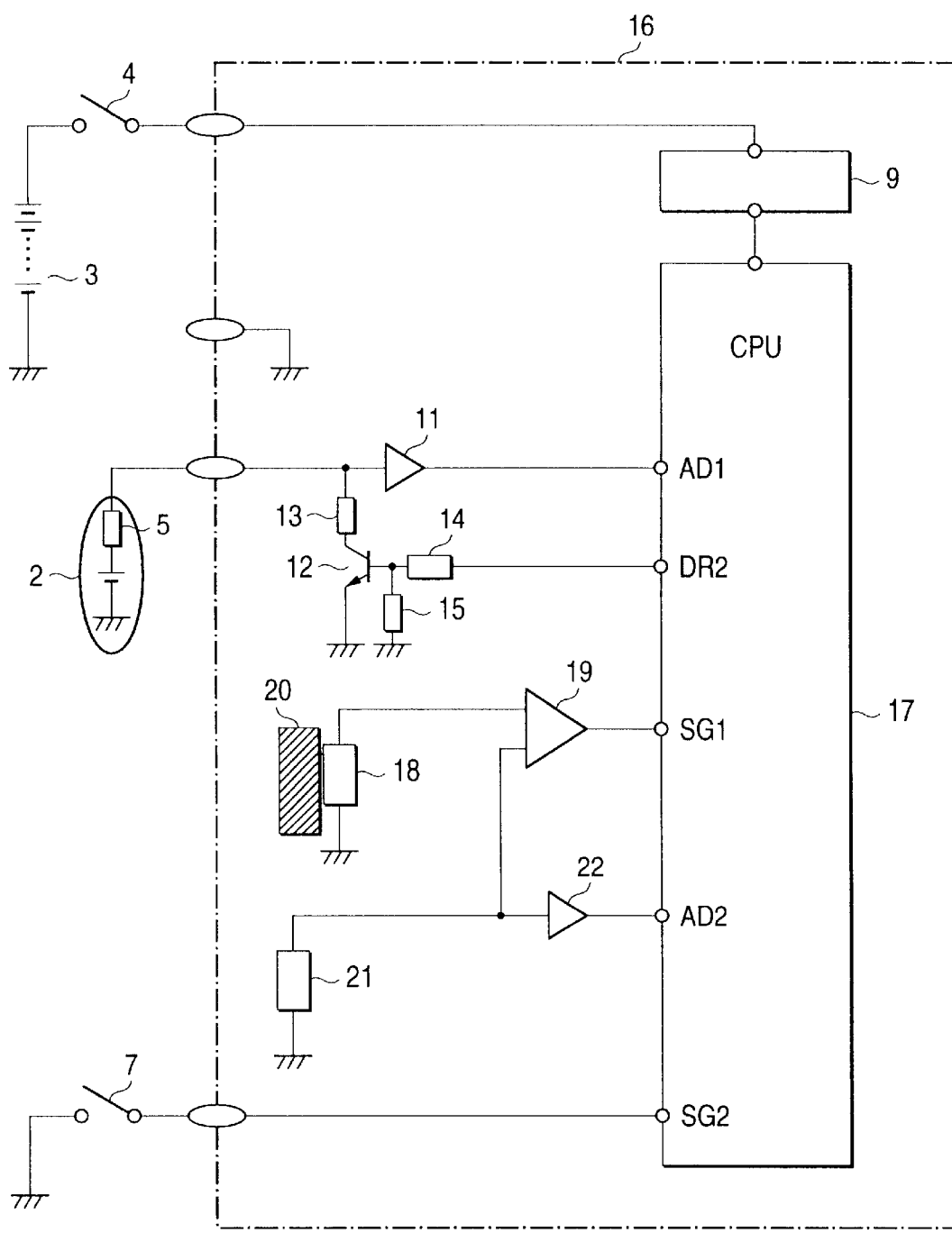
FIG. 3 is a circuit diagram of a temperature detector for an exhaust gas sensor of Embodiment 2 of the present invention.

FIG. 3 is a circuit diagram of the temperature detector for an exhaust gas sensor of Embodiment 2 of the present invention. Like reference characters are used to indicate like parts in Embodiments 1 and 2. In FIG. 3, reference numeral 16 is a temperature detector for detecting the temperature of the exhaust gas sensor 2 and controlling a heater not shown which is incorporated into the exhaust gas sensor 2. Reference numeral 3 is a battery mounted on a vehicle and used for feeding electrical power to the temperature detector 16. Reference numeral 4 is a key switch. Reference numeral 5 is an internal resistance which is schematically illustrated. Reference numeral 7 is a mode switch for switching the temperature detector 16 between the practical operation mode and the test mode. This test mode is used when the temperature detector 16 itself is inspected in the delivery inspection.

Reference numeral 17 is CPU that is a control means arranged in the temperature detector 16. Reference numeral 9 is a constant voltage power source for supplying a constant voltage, for example, for supplying a constant voltage of DC 5V to CPU 17. Reference numeral 11 is an amplifier for amplifying an output of the exhaust gas sensor 2 and inputting it into input terminal AD1 for A/D conversion of CPU 17. Reference numeral 12 is a transistor for detecting internal resistance which is driven by a signal sent from output terminal DR2 of CPU 17, wherein this transistor 12 connects a load resistance 13 with the exhaust gas sensor 2. Reference numeral 14 is a base resistance of the transistor 12 arranged in a signal path from output terminal DR2 of CPU 17. Reference numeral 15 is a ballast resistance arranged between the base of the transistor 12 and the emitter.

Reference numeral 18 is a first temperature sensor connected with signal input terminal SG1 of CPU 17 via the comparator 19. The first temperature sensor 18 detects a surface temperature of the heat sink 20 which radiates the heat generated from heating parts such as an electrical power source of the temperature detector 16 and a power transistor not shown in the drawing. Reference numeral 21 is a second temperature sensor arranged on a surface of the temperature detector 16 so as to detect the environmental temperature of the temperature detector 16. An output of the second temperature sensor 21 is inputted into input terminal AD2 of CPU used for conversion of A/D via the amplifier 22 and at the same time inputted into one of the input terminals of the comparator 19.

In the above temperature detector for an exhaust gas sensor of Embodiment 2 of the present invention, CPU is operated in the same manner as that shown on the flow chart of Embodiment 1 shown in FIG. 2. However, the following difference is made in operation because of the difference of hardware. In step 106 shown on the flow chart of FIG. 2, detection of a long stoppage of the internal combustion engine is judged by the output of the counter 10 used for the timer. However, in this embodiment, detection of a long stoppage of the internal combustion engine is judged as follows. When the key switch 4 closes the circuit at the start of operation, outputs of the temperature sensors 18, 21 are inputted into the comparator 19. When temperatures of both temperature sensors 18, 21 are substantially the same, the logical output of the comparator 19 becomes level L, which is inputted into signal input terminal SG1 of CPU 17.

When the time of stop of operation of the internal combustion engine is longer than a predetermined time and the surface temperature of the heat sink 20, which requires a long period of time to radiate heat, is substantially equal to the environmental temperature, it is judged that the temperature of the exhaust gas sensor 2 is also substantially equal to the environmental temperature. In Embodiment 1, the environmental temperature is measured in such a manner that the outside air temperature of the internal combustion engine and the temperature of cooling water are measured by the temperature sensor 6. However, in this embodiment, the environmental temperature of the temperature detector 16 is measured by the temperature sensor 21. After the internal combustion engine has been stopped over a long period of time and when the logical output of the above comparator 19 is at level L, the output of the temperature sensor 18 can be made to be the environmental temperature.

In this connection, when the temperature detector 16 and the exhaust gas sensor 2 are arranged at positions, the environmental temperatures of which are different from each other, for example, when the temperature detector 16 and the exhaust gas sensor 2 are respectively arranged inside and outside the vehicle, the temperature difference can be corrected by CPU 17. In the case where it is impossible to estimate the time of stop of operation by the time constant of radiation, for example, in the case where the time constant of radiation of the heat sink 20 and that of the exhaust gas sensor 2 are different from each other, the latest values of the past several times are stored in step 109 shown in FIG. 2, and the judgment can be conducted by using the average of these values. In the case where there is a big difference between the read value of this time and the read value of the last time, the read value of this time is neglected and the average value is used for judgment.

As explained above, according to the temperature detector for an exhaust gas sensor of the present invention, after the detection of the period in which the operation of an internal combustion engine is stopped, the value of internal resistance and the environmental temperature of the exhaust gas sensor are measured and renewed at each starting time of operation, and the characteristic of the internal resistance versus the temperature is made from the value of internal resistance and the environmental temperature and the thus made characteristic is stored, and the temperature of the exhaust gas sensor at the present time is calculated from the value of internal resistance and the characteristic of the internal resistance versus the temperature which are measured during the operation. Therefore, the temperature can be always detected without being affected by the fluctuation and the change with age.

The value of internal resistance of the exhaust gas sensor at the first motion in the practical operation is stored as a reference value and compared with the value of internal resistance after the stop of operation which is longer than a predetermined period of time, and when the difference is more than a predetermined value, it is judged that the deterioration has been caused and a warning is given.

Therefore, the deterioration of the exhaust gas sensor can be found in its early stages. Further, the outside air temperature sensor and the cooling water temperature sensor, which are already provided, are used as the temperature sensor, and the digital clock mounted on the vehicle is used as the timer, and the heat radiating time of the heat radiating parts is used. Therefore, the structure of hardware can be simplified and the size of the device can be reduced. In this way, the present invention can provide an excellent temperature detector for an exhaust gas sensor.

What is claimed:

1. A temperature detector comprising:

an exhaust gas sensor for detecting a concentration of oxygen contained in exhaust gas discharged from an internal combustion engine;

a temperature sensor for measuring an environmental temperature being substantially the same as the exhaust gas sensor;

a resistance detector for measuring an internal resistance value of the exhaust gas sensor;

a timer for measuring an operation stop time of the internal combustion engine; and a controller for detecting the internal resistance value of the exhaust gas sensor and the environmental temperature at each operation starting point when a period of operation stop conducted by the timer is longer than a predetermined period, the controller for calculating a characteristic of the internal resistance value versus the temperature of the exhaust gas sensor from both of the internal resistance of the exhaust gas sensor and the environmental temperature, the controller for renewing and storing the characteristic of the internal resistance value versus the temperature of the exhaust gas sensor, the controller for calculating a temperature of the exhaust gas sensor from the internal resistance of the exhaust gas sensor in operation and from the characteristic in operation of the internal resistance value versus the temperature of the exhaust gas sensor.

2. The temperature detector according to claim 1, wherein the controller has a discriminating function to discriminate an operation state between a test mode and an operation mode;

the controller stores the internal resistance of the exhaust gas sensor measured in a first motion of the operation mode after the completion of the test mode, as a reference value; and deterioration of the exhaust gas sensor is judged when the reference value is compared with the internal resistance value of the exhaust gas sensor measured at each operation staring point.

3. The temperature detector for an exhaust gas sensor according to claim 1, wherein the temperature sensor is an outside air temperature sensor mounted on a vehicle or a cooling water temperature sensor.

4. The temperature detector for an exhaust gas sensor according to claim 1, wherein the timer utilizes a signal obtained from a digital clock mounted on a vehicle.

5. The temperature detector for an exhaust gas sensor according to claim 1, wherein the timer utilizes a heat-radiating time in which heat is radiated so that a heating section of the temperature detector is cooled to a predetermined temperature after the stop of operation.

* * * * *